United States Patent [19]

Dürr et al.

[11] 4,349,377
[45] Sep. 14, 1982

[54] PHENOXYPHENYLTHIOALKANECAR-BOXYLIC ACID AMIDES AND THEIR USE AS HERBICIDES AND PLANT GROWTH REGULANTS

[75] Inventors: Dieter Dürr, Bottmingen; Otto Rohr, Therwil, both of Switzerland; Georg Pissiotas, Lörrach, Fed. Rep. of Germany; Beat Böhner, Binningen, Switzerland

[73] Assignee: Ciba-Geigy Corporation, Ardsley, N.Y.

[21] Appl. No.: 184,608

[22] Filed: Sep. 5, 1980

Related U.S. Application Data

[60] Division of Ser. No. 55,675, Jul. 9, 1979, abandoned, which is a continuation-in-part of Ser. No. 921,931, Jul. 3, 1978, abandoned.

[30] Foreign Application Priority Data

Jul. 7, 1977 [CH] Switzerland .......................... 8426/77
Jan. 27, 1978 [CH] Switzerland .......................... 9261/78

[51] Int. Cl.³ .................... A01N 31/08; C07C 103/22
[52] U.S. Cl. .......................................... 71/98; 71/76; 71/78; 260/453 RW; 260/465 D; 544/159; 560/9; 560/17; 564/162
[58] Field of Search .............................. 71/98, 118, 76; 564/162, 161

[56] References Cited

U.S. PATENT DOCUMENTS 3,784,635 1/1974 Theissen ....................... 260/471 R
3,954,442 5/1976 Becker et al. ...................... 71/108
4,070,177 1/1978 Nishiyama et al. ................. 71/105

*Primary Examiner*—Catherine L. Mills
*Attorney, Agent, or Firm*—Frederick H. Rabin

[57] ABSTRACT

This invention relates to new phenoxyphenylthioalkanecarboxylic acid derivatives with herbicidal and plant growth-regulating activity of the formula

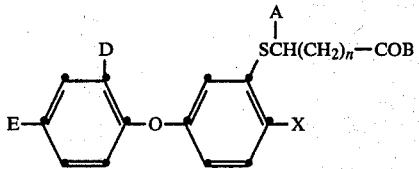

wherein A is hydrogen or $C_1$–$C_4$alkyl, B is a salt of a carboxylic-acid, an ester, a thioester, an amide or an imidoether thereof, X is hydrogen, halogen, cyano, $C_1$–$C_4$alkyl or $C_1$–$C_4$alkoxy, D is hydrogen, halogen, cyano or trifluoromethyl, E is halogen, cyano, nitro or trifluoromethyl and N is 0 or 1.

6 Claims, No Drawings

PHENOXYPHENYLTHIOALKANECARBOXYLIC ACID AMIDES AND THEIR USE AS HERBICIDES AND PLANT GROWTH REGULANTS

CROSS REFERENCE TO RELATED APPLICATION

This is a division of application Ser. No. 055,675 filed on July 9, 1979, which is a continuation-in-part of application Ser. No. 921,931, filed on July 3, 1978, both now abandoned.

DETAILED DISCLOSURE

The present invention relates to novel phenoxyphenylthioalkanecarboxylic acid derivatives, which have a herbicidal and plant growth-regulating activity, herbicidal and plant growth-regulating compositions which contain them as active ingredients, and the use of the novel compounds, or of compositions containing them, as herbicides and/or for regulating plant growth.

The novel phenoxyphenylthioalkanecarboxylic acid derivatives have the formula I

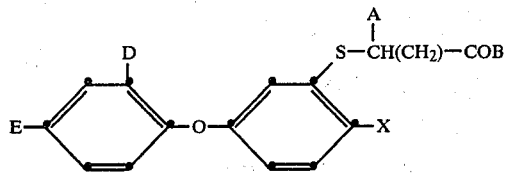

wherein A is hydrogen or $C_1$–$C_4$alkyl, B is a radical —$OR_1$, $SR_1$, —$NR_2R_3$ or O—N=$C(CH_3)_2$, X is hydrogen, halogen, cyano, $C_1$–$C_4$alkyl or $C_1$–$C_4$alkoxy, D is hydrogen, halogen, cyano, nitro or trifluoromethyl, E is halogen, cyano, nitro or trifluoromethyl, n is 0 or 1, $R_1$ is the cation of an alkali metal, a quaternary ammonium group $NR_aR_bR_cR_d$, wherein $R_a$ to $R_d$ represent hydrogen, $C_1$–$C_6$-alkyl, optionally substituted by optionally interrupted by oxygen, or substituted by hydroxyl, halogen or cyano, or benzyl, $R_1$ and $R_2$ are hydrogen, $C_1$–$C_{18}$alkyl which may be interrupted by oxygen, sulfur or an imino group or substituted by hydroxyl, halogen, or cyano, $C_3$–$C_6$ alkenyl optionally substituted by halogen $C_3$–$C_6$ alkenyl, $C_3$–$C_6$-cycloalkyl, phenyl or benzyl, optionally substituted by halogen, cyano, nitro, trifluoromethyl, $C_1$–$C_4$alkyl, $C_1$–$C_4$alkoxy or $C_1$–$C_4$-alkylthio, $R_3$ is hydrogen, $C_1$–$C_4$alkyl, $C_1$–$C_4$alkoxy or $C_3$–$C_6$alkenyl, $R_2$ and $R_3$ together with the nitrogen atom to which they are bound, may also form a pyrrolidine, piperpyrrolidine, piperidine, pyridine, morpholine or piperazinyl ring, which is optionally substituted by $C_1$–$C_4$alkyl or phenyl in the case of piperazine.

The compounds of the present invention have a low toxicity to warmblooded animals and their application causes no problems. They are stable compounds which are soluble in the conventional organic solvents, such as alcohols, ketones, dimethyl formamide, dimethyl sulphoxide. Ordinarily, rates of application between 0.1 and 5 kg per hectare are required.

The active compounds of the formula (I) of the present invention possess a herbicidal action, especially in pre- and post-emergent application, and can be used as weed-killers in crops of mono- and dicotyledonous plants. They are also possess advantageous growth-regulating effects (growth inhibition). In particular, they inhibit the growth of dicotyledonous plants. Exemplary of the useful application of the compounds of the present invention are:

the reduction of the vegetative growth in soya and similar leguminosae, resulting in an increase in the yield of these plants;

the inhibition of the undesirable growth of suckers in tobacco plants, the leading shoots of which have been cut, thus promoting the formation of larger and finer leaves;

the inhibition of the growth of grass and dicotyledonous plants, such as fruit trees, ornamental trees, bushes and hedgerows, with the object of saving cutting work.

Good activity showed these compounds of formula I, wherein R is $OR_1$. $R_1$ is an alkali metal cation or a quaternary ammonium group $NR_a$, $R_b$, $R_c$, $R_d$ as defined under Formula I, —hydrogen, —$C_1$–$C_{18}$alkyl, optionally interrupted by oxygen, sulfur or an imino group, or substituted by hydroxyl, halogen or cyano, —$C_3$–$C_6$alkenyl, optionally substituted by halogen and A, X, D, E and n have the meaning given under formula I. Equally good herbicidal activity was observed when using the compounds of formula I, wherein B is $NR_2R_3$ and A, X, D, E, n, $R_2$ and $R_3$ have the meaning given under formula I.

The novel compounds of the formula I may be obtained by methods which are known, for example in accordance with one of the following reaction schemes,

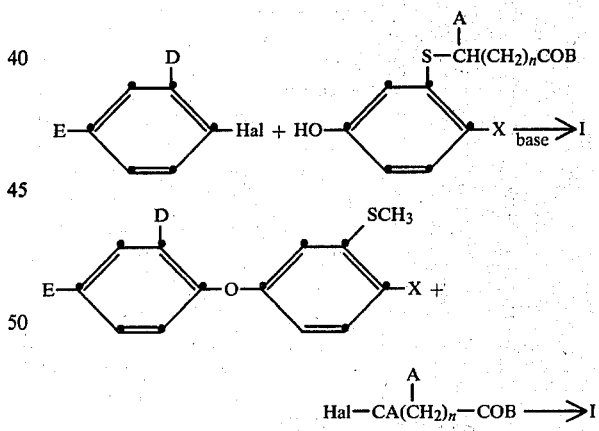

or by esterification or transformation into a salt or an amide of a compound of the formula I, claim 1 wherein B is the hydroxyl group.

n the above formulae, A, B, X, D, E, and n are as defined in formula I, Hal is a halogen atom.

A few of these starting compounds and processes for their production are known and described for example in German Offenlegungsschriften Nos. 2,130,919 or 2,333,848.

In recent years there has appeared an extensive patent literature on variously substituted diphenyl ethers which are herbicidally active. A number of isolated phenoxyphenylthioalkanecarboxylic acid derivatives have also become known, cf. German Offenlegungsschrift Nos. 2,223,894.

However, the herbicidal action of the known phenoxyphenylthioalkanecarboxylic acid derivatives, especially in low rates of concentration, is unsatisfactory.

It has now surprisingly been found that the novel compounds of the formula I possess strong herbicidal properties, especially also selective herbicidal activity.

The following Examples illustrate in more detail the methods of obtaining the active compounds of the formula I. Further active compounds prepared in corresponding manner are listed in the subsequent tables. Percentages are by weight. Boiling points, made under reduced pressure are given with indication of temperature and pressure in millibar (mbar).

EXAMPLE 1

3-(2',4',-Dichlorophenoxy)-6-cyano-phenylthioacetic acid methyl ester

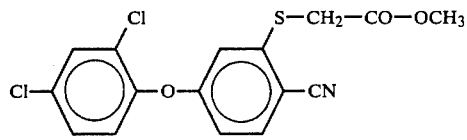

(a) 12 g of 4-chloro-2-methylmercapto-nitrobenzene are heated to 160° C. in 50 ml of dimethyl sulphoxide with 10 g of 2,4-dichlorophenol and 2.5 g of sodium hydroxide. After two hours, the batch is poured onto ice and extracted with ethyl acetate. The organic solution is concentrated and the residue recrystallised from toluene/hexane, affording 16 g of 2,4-dichloro-3'-methylmercapto-4'-nitrodiphenyl ether with a melting point of 120°–122° C. The catalytic reduction in dioxane with Raney nickel affords 2,4-dichloro-3'-methylmercapto-4'-amino-diphenyl ether in virtually quantitative yield. Melting point: 40°–43° C.

(b) 65 g of this compound are mixed with 300 ml of water and 144 ml of conc. sulphuric acid and the mixture is cooled to 0° C. By reaction with a 5% sodium nitrite solution at 0° to 5° C. a diazonium salt solution is prepared, to which a solution of 39.5 g of potassium iodide in 370 ml of water is added dropwise at 0° C. after 1 hour. A tacky precipitate forms, which is dissolved after 2 hours by addition of methylene chloride. The organic phase is separated and concentrated. The residue is extracted repeatedly with warm hexane and the combined hexane extracts are concentrated and cooled. Crystallisation yields 67 g of 2,4-dichloro-3'-methylmercapto-4-iodo-diphenyl ether.

(c) 15 g of this compound are stirred in 50 ml of N-methyl-2-pyrrolidone at 140° C. with 3.5 g of copper (I) cyanide in a nitrogen atmosphere. After 3 hours the reaction mixture is cooled and stirred with 500 ml of water and 20 ml of conc. ammonia. The precipitate is collected, dried and recrystallised from toluene/hexane, affording 10 g of 2,4-dichloro-3'-methylmercapto-4'-cyano-diphenyl ether with a melting point of 84° C.

(d) 5 g of this compound are refluxed in 20 ml of methyl bromoacetate. After 8 hours the methyl bromoacetate is distilled off and the residue is purified by chromatography, yielding the title compound with a melting compound of 95° C., together with unreacted starting material.

EXAMPLE 2

3-(2',4'-Dichlorophenoxy)-6-iodo-phenylthioacetic acid methyl ester

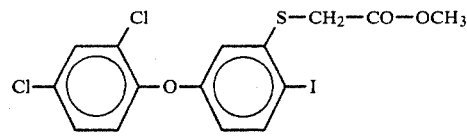

10 g of 2,4-dichloro-3'-methylmercapto-4'-iodo-diphenyl ether and 20 ml of methyl bromoacetate are refluxed for 10 hours, then purification is effected by chromatography on a column of silica gel with cyclohexane as eluant. The solvent is evaporated off, affording 7 g of a clear oil with a refractive index $n_D^{24}$: 1.6528.

EXAMPLE 3

β-[3-(2'-Chloro-4-trifluoromethylphenyl)-phenylthio] propionic acid ethyl ester

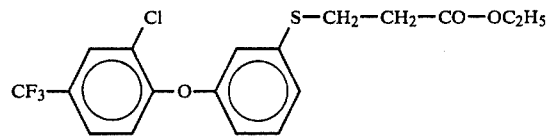

71 g of 3-methylmercaptophenol, 118.5 g of 3,4-dichlorobenzotrifluoride and 22.5 g of sodium hydroxide are reacted in 400 ml of dimethyl sulphoxide for 4 hours at 140° C. The reaction mixture is then poured onto ice. The precipitated oil is taken up in ether and purified by distillation. 32 g of the resulting 4-trifluoromethyl-2-chloro-3'-methylmercapto-diphenyl ether obtained in good yield (boiling point 115°–120° C./0.02 torr) are stirred with 90 g of ethyl 3-bromopropionate and a crystal of potassium iodide for 10 hours at 170° C. Working up is via distillation, yielding the title compound in addition to unreacted starting material. Boiling point: 250° C./0.03 torr in a bulb tube.

EXAMPLE 4

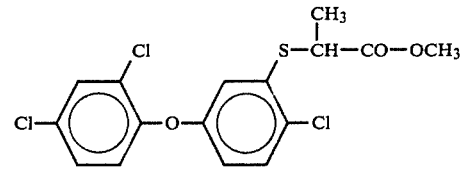

α-[3-(2',4'-Dichlorophenoxy)-6-chlorophenylthio] propionic acid methyl ester (a) To a solution of 400 g of di-(2',4'-dichlorophenoxy)-nitrobenzene, 64 g of 85% potassium hydroxide and 700 ml of dioxane are added 45 g of methylene mercaptan at 50°–70° C. After 1 hour the solvent is stripped off in vacuo and the residue is taken up in toluene. The solution freed from 2,4-dichlorophenol by washing with dilute sodium hydroxide solution is added dropwise to a boiling mixture of 500 g of iron powder, 500 g of ethanol and 50 ml of conc. hydrochloric acid. After refluxing for 15 hours, the batch is made alkaline with 30% sodium hydroxide solution, iron sludge is removed by suction filtration and the filter cake is washed with toluene. The organic phase of the filtrate is concentrated and distilled, affording 192.5 g of 2,4-dichloro-3'-methylthio-4'-amino-diphenyl ether with a boiling point of 170° C./0.1 mbar.

(b) 180 g of the above amino-compound are dissolved in 1.5 liters of glacial acetic acid and 153 ml of hydrochloric acid are added to the solution. A diazo solution is prepared by the dropwise addition of a solution of 41.5 g of sodium nitrite in 100 ml of water at 5° C. After destroying excess nitrite with sulphamic acid, the diazo solution is added dropwise at 75°–90° C. to 2 liters of 18% hydrochloric acid and 118 g of copper (I) chloride. After 1 hour the batch is extracted with toluene and the organic phase is concentrated. Distillation of the residue yields 172 g of 3-(2',4'-dichlorophenoxy)-6-chloromethylmercaptobenzene with a boiling point of 158° C./0.05 mbar.

(c) 140 g of the above compound are refluxed for 16 hours with 105 ml of methyl 2-bromopropionate and a crystal of potassium iodide. The subsequent distillation yields 150 g of the title compound with a boiling point of 186° C./0.09 mbar.

EXAMPLE 5

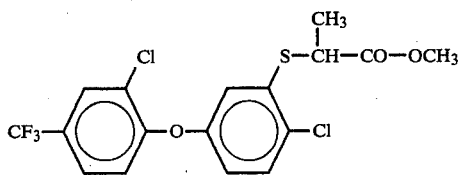

α-[3-(2'-chloro-4'-trifluoromethylphenoxy)-6-chlorothio] propionic acid methyl ester (a) With efficient stirring, 241 g of 2-chloro-5-methoxyaniline are added to 310 ml of water and 385 ml of conc. hydrochloric acid, followed by the addition of 750 g of ice. The mixture is cooled to −10° C. and a solution of 111 g of sodium nitrite in 150 ml of water are added all at once, whereupon the temperature rises to 10° C. After 30 minutes excess nitrite is destroyed with sulphamic acid and the solution is clarified by filtration. This diazo solution is added dropwise at 55°–60° C. to a solution of 300 ml of water, 800 ml of toluene, 225 g of potassium methylxanthogenate, 85 g of sodium bicarbonate and 75 ml of 30% sodium hydroxide solution. When the very vigorous evolution of gas has ceased the organic phase is separated, washed with water, dried over sodium sulphate and added dropwise to 100 ml of triethylamine at 70° C. After refluxing for 2 hours, cooling, and adding 200 ml of 30% sodium hydroxide solution, the organic phase is separated and distilled, affording 160 g of 4-chloro-3-methylmercaptoanisole with a boiling point of 138°–145° C./11 mbar.

152.2 g of this compound are saponified to 110 g of 4-chloro-3-methylmercaptophenol by a procedure analogous to that described in J. Am. Chem. Soc. 79, 720. Boiling point: 117°–121° C./0.03 mbar.

(b) 50 g of 4-chloro-3-methylmercaptophenol, 62 g of 3,4-dichlorobenzotrifluoride and 12 g of sodium hydroxide are stirred in 150 ml of dimethyl sulphoxide for 6 hours at 142° C. The reaction mixture is then poured onto ice and extracted with toluene. Distillation of the organic phase yields 81 g of 3-(2'-chloro-4'-trifluoromethylphenoxy)-6-chlorothioanisole with a boiling point of 158° C./0.4 mbar.

20 g of this compound are stirred with 30 ml of methyl 2-bromopropionate for 20 hours at 190° C., followed by distillation in a bulb tube.

Yield: 21 g of α-[3-(2'-chloro-4'-trifluoromethylphenoxy)-6-chlorophenylthio] propionic acid methyl ester. Boiling point: 200° C./0.13 mbar.

EXAMPLE 6

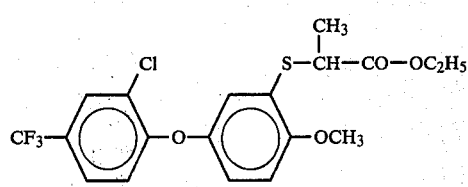

α-[3-(2'-Chloro-4'-trifluoromethylphenoxy)-6-methoxythio] propionic acid methyl ester (a) 187 g of hydroquinone monomethyl ether, 324 g of 3,4-dichlorobenzotrifluoride and 60 g of sodium hydroxide are stirred in 500 ml of dimethyl formamide for 5 hours at 140° C. The reaction mixture is poured onto ice and the precipitated 2-chloro-4-trifluoromethyl-4'-methoxydiphenyl ether is collected with suction. 315 g of this compound (m.p. 60°–63° C.) are treated dropwise at 10° C. in 1 liter of glacial acetic acid with 170 g of mixed acid consisting of 67 g of fuming nitric acid and 103 g of conc. sulphuric acid. The batch is stirred for 3 hours and the precipitate is then collected with suction and dried, affording 291 g of 4-(2'-chloro-4'-trifluoromethyl-phenoxy)-2-nitro-anisole with a melting point of 90°–92° C.

(b) 318 g of the above nitro-compound are hydrogenated in dioxane with nickel as catalyst. The catalyst is separated and the reaction solution concentrated. Yield: 300 g of 4-(2'-chloro-4'-trifluoromethyl-phenoxy)-2-amino-anisole. Boiling point: 185° C./0.4 (distillation in a bulb tube); melting point: 36°–38° C.

(c) 97 g of the above amino-compound are diazotised in 100 ml of dimethyl formamide, 100 ml of conc. hydrochloric acid and 100 ml of water with sodium nitrite in accordance with Example 4(a), and the diazo solution is reacted with potassium methylxanthogenate to give 4-(2'-chloro-4'-trifluoromethyl-phenoxy)-2-methylmercapto-anisole. Boiling point: 150°–155° C./0.01 mbar.

(d) 8 g of the above compound are reacted with ethyl 2-bromopropionate as in Example 4(c), yielding the title compound. Boiling point: 190° C./0.001 mbar (distillation in a bulb tube).

In accordance with these Examples, the following compounds were prepared:

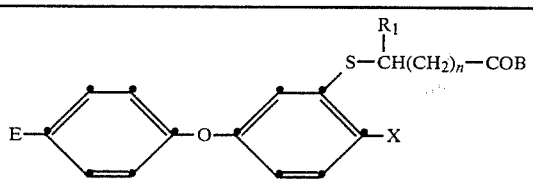

| No. | E | D | X | R₁<br>$CH(CH_2)_n$ | B | physical constant |
|---|---|---|---|---|---|---|
| 1 | Cl | Cl | CN | $CH_2$ | $OCH_3$ | m.p. 40–43° |
| 2 | Cl | Cl | I | $CH_2$ | $OCH_3$ | $n_D^{24}$ 1.6528 |
| 3 | $CF_3$ | Cl | H | $C_2H_4$ | $OC_2H_5$ | b.p. 250°/0,03 mbar |
| 4 | Cl | Cl | Cl | $CH(CH_3)$ | $OCH_3$ | b.p. 136°/0.09 mbar |
| 5 | $CF_3$ | Cl | $OCH_3$ | $CH(CH_3)$ | $OC_2H_5$ | b.p. 200°/0.13 mbar |
| 6 | $CF_3$ | Cl | Cl | $CH(C_2H_5)$ | $OC_2H_5$ | b.p. 155°/0.01 mbar |
| 7 | $CF_3$ | CN | Cl | $CH(CH_3)$ | $OCH_3$ | b.p. 195°/0.01 mbar |
| 8 | $CF_3$ | Cl | $OCH_3$ | $CH(CH_3)$ | $O_nC_{18}H_{37}$ | |
| 9 | Cl | Cl | — | $CH(CH_3)$ | $OCH_3$ | |
| 10 | Cl | Cl | $CH_3$ | $CH(CH_3)$ | $OCH_3$ | |
| 11 | Cl | Cl | $CH_3$ | $CH(CH_3)$ | $OCH_3$ | $n_D^{23}$ 1.5960 |
| 12 | $CF_3$ | Cl | $CH_3$ | $CH(CH_3)$ | $OCH_3$ | b.p. 165°/0.001 mbar |
| 13 | $CF_3$ | Cl | CN | $CH(CH_3)$ | $OCH_3$ | |
| 14 | $CF_3$ | Cl | Br | $CH(CH_3)$ | $NHC_2H_4OCH_3$ | |
| 15 | $CF_3$ | Cl | Cl | $CH_2$ | $OCH_3$ | b.p. 190°/0.5 mbar |
| 16 | $CF_3$ | $NO_2$ | H | $CH(C_2H_5)$ | $OC_2H_5$ | b.p. 185°/0,05 mbar |
| 17 | $CF_3$ | $NO_2$ | H | $CH(CH_3)$ | $OC_2H_5$ | |
| 18 | Cl | $NO_2$ | H | $C_2H_4$ | $N(C_2H_5)_2$ | |
| 19 | Cl | $NO_2$ | $OCH_3$ | $CH(CH_3)$ | $OCH_3$ | |
| 20 | Cl | $CF_3$ | H | $CH(C_2H_5)$ | $O_nC_4H_9$ | |
| 21 | Cl | Cl | CN | $CH_2$ | ONa | |
| 22 | Cl | Cl | I | $CH_2$ | $ONH(CH_3)_3$ | |
| 23 | Cl | Cl | Cl | $C_2H_4$ | $OCH_3$ | $n_D^{24}$ 1.6059 |
| 24 | Cl | Cl | Cl | $CH_2$ | $OCH_3$ | b.p. 230°/0.01 mbar |
| 25 | Cl | Cl | Cl | $CH(CH_3)$ | $OC_2H_4N(CH_3)_2$ | |
| 26 | Cl | Cl | H | $C_2H_4$ | $OCH_3$ | $n_D^{23}$ 1.5972 |
| 27 | Cl | Cl | I | $CH(CH_3)$ | $OC_2H_5$ | $n_D^{23}$ 1.6185 |
| 28 | $CF_3$ | Cl | H | $CH(CH_3)$ | $OCH_3$ | b.p. 140°/0.08 mbar |
| 29 | $CF_3$ | Cl | H | $C_2H_4$ | $OCH_2OCH_3$ | |
| 30 | $CF_3$ | $NO_2$ | Cl | $CH_2$ | $OCH_3$ | b.p. 235°/0.5 mbar |
| 31 | $CF_3$ | $NO_2$ | Cl | $CH(CH_3)$ | $OCH_3$ | b.p. 235°/0.45 mbar |
| 32 | $CF_3$ | Cl | Cl | $CH(CH_3)$ | $ONH_3C_2H_4OH$ | |
| 33 | $CF_3$ | Cl | $OCH_3$ | $CH(CH_3)$ | $OCH_3$ | b.p. 195°/0.04 mbar |
| 34 | Cl | Cl | Cl | $CH(C_2H_5)$ | $OC_2H_5$ | b.p. 185°/0.02 mbar |
| 35 | Cl | Cl | Cl | $CN(CH_3)$ | $N(CH_3)OCH_3$ | |
| 36 | $CF_3$ | Cl | $CH_3$ | $CH(CH_3)$ | $OC_2H_4CN$ | |
| 37 | $CF_3$ | Cl | Cl | $CH(CH_3)$ | $SCH_3$ | |
| 38 | Cl | Cl | $CH_3$ | $CH(CH_3)$ | $OC_2H_4Cl$ | |
| 39 | Cl | $NO_2$ | $OCH_3$ | $CH(CH_3)$ | $ON=C(CH_3)_2$ | |
| 40 | Cl | Cl | Cl | $CH(CH_3)$ | $OCH_2-C\equiv CH$ | |
| 41 | $CF_3$ | Cl | CN | $CH(CH_3)$ | O—furyl | |
| 42 | Cl | Cl | Br | $CH(CH_3)$ | $ONH_4$ | |
| 43 | Br | Br | Cl | $CH(CH_3)$ | —N(morpholino)O | |
| 44 | $CF_3$ | Cl | Cl | $CH(CH_3)$ | $NHC_2H_4OCH_3$ | b.p. 250°/0.02 mbar |

-continued

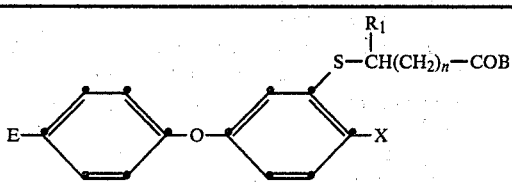

| No. | E | D | X | $R_1$<br>$\|$<br>$CH(CH_2)_n$ | B | physical constant |
|---|---|---|---|---|---|---|
| 45 | Cl | Cl | Cl | $CH(CH_3)$ | $OCH-CH=CH_2$ | $n_D^{24}$ 1.5968 |
| 46 | $CF_3$ | Cl | 4-Cl | $CH(CH_3)$ | $OCH_3$ | b.p. 160°/ 0.2 mbar |
| 47 | Cl | Cl | Cl | $CH(CH_3)$ | $O_nC_4H_9$ | b.p. 230°/ 0.001 mbar |
| 48 | Cl | Cl | $OCH_3$ | $CH_2$ | $OCH_3$ | |
| 49 | Cl | Cl | Cl | $C_2H_4$ | $OCH_3$ | $n_D^{23}$ 1.5820 |
| 50 | Cl | Cl | Cl | $CH(CH_3)$ | $OCH_2CN$ | b.p. 245°/ 0.03 mbar |
| 51 | $CF_3$ | Cl | H | $CH_2$ | $OCH_3$ | m.p. 93–94° |
| 52 | Cl | Cl | Cl | $CH(CH_3)$ | $OCH_3$ | $n_D^{24}$ 1.5942 |
| 53 | Cl | Cl | Cl | $CH(CH_3)$ | $NHC_2H_4OH$ | $n_D^{23}$ 1.5865 |
| 54 | Cl | Cl | Cl | $CH(CH_3)$ | $NHC_2H_4OCH_3$ | $n_D^{24}$ 1.5941 |
| 55 | Cl | Cl | Br | $CH_2$ | $OCH_3$ | oil (viscous) |
| 56 | Cl | Cl | Br | $CH(CH_3)$ | $OCH_3$ | b.p. 240°/ 0.06 mbar |
| 57 | Cl | Cl | Cl | $CH(CH_3)$ | OH | m.p. 119–121° |
| 58 | $CF_3$ | CN | Cl | $CH_2$ | $OCH_3$ | m.p. 85–87° |

The novel active compounds of the formula I are stable compounds which are soluble in conventional organic solvents, such as alcohols, ethers, ketones, dimethyl formamide, dimethyl sulphoxide etc.

The compositions of the present invention are obtained in known manner by homogeneously mixing and grinding active substances of the general formula I with suitable carriers, with or without the addition of dispersants or solvents which are inert to the active substances. The active substances can be processed to the following formulations:
solid formulations:
 dusts, tracking powders, granules (coated granules, impregnated granules and homogeneous granules);
active substance concentrates which are dispersible in water:
 wettable powders, pastes, emulsions; liquid formulations: solutions.

The concentration of active substance in the compositions of the present invention is from 1 to 80% by weight and can also be as low as about 0.05 to 1% by weight. The compositions of the invention can also be mixed with other biocidal active substances or compositions.

The active substances (compounds) of the formula I can be formulated for example as follows (parts are by weight):

Emulsifiable Concentrate

The following ingredients are mixed to prepare 25% emulsion concentrate:
25 parts of an active substance of the formula I
5 parts of a mixture of nonylphenolpolyoxyethylene and calcium dodecylbenzenesulphonate,
15 parts of cyclohexanone,
55 parts of xylene.
This concentrate can be diluted with water to give emulsions in suitable concentrations of e.g. 0.1 to 10%. Such emulsions are suitable for controlling weeds in cultivations of plants.

Granules

The following substances are used to prepare a 5% granulate:
5 parts of one of the active substances of the formula I,
0.25 parts of epichlorohydrin,
0.25 parts of cetyl polyglycol ether,
3.50 parts of polyethylene glycol,
91 parts of kaolin (particle size 0.3–0.8 mm).
The active substance is mixed with epichlorohydrin and dissolved with 6 parts of acetone, and the polyethylene glycol and cetyl polyglycol ether are then added. The resultant solution is sprayed on kaolin and subsequently evaporated in vacuo.

Wettable Powder

The following constituents are used to prepare (a) a 70% and (b) a 10% wettable powder:
(a)
 70 parts of an active substance of the formula I,
 5 parts of sodium dibutylnaphthalene sulphate,
 3 parts of naphthalenesulphonic acid/phenolsulphonic acid/formaldehyde condensate (3:2:1),
 10 parts of kaolin,
 12 parts of Champagne chalk;
(b)
 10 parts of an active substance of the formula I,
 3 parts of a mixture of the sodium salts of saturated fatty alcohol sulphates,
 5 parts of naphthalenesulphonic acid/formaldehyde condensate,
 82 parts of kaolin.
The respective active substance is applied to the corresponding carriers (kaolin and chalk) and then these are mixed and ground, to yield wettable powders of excellent wettability and suspension powder. By diluting these wettable powders with water it is possible to obtain suspensions containing 0.1 to 8% of active substance. These suspensions are suitable for controlling weeds in cultivations of plants.

Paste

The following substances are used to prepare a 45% paste:
   45 parts of an active substance of the formula I
   5 parts of sodium aluminium silicate,
   14 parts of cetyl polyglycol ether with 8 moles of ethylene oxide,
   1 part of oleyl polyglycol ether with 5 moles of ethylene oxide,
   2 parts of spindle oil,
   10 parts of polyethylene glycol,
   23 parts of water.

The active substance is intimately mixed with the adjuvants in appropriate devices and ground. A paste is obtained from which, by dilution with water, it is possible to prepare suspensions of the desired concentration of active substance.

The novel 3-phenoxy-α-phenylthioalkanecarboxylic acid derivatives of the formula I and the compositions which contain them have an excellent selective herbicidal action against grass-like weeds in different crops of cultivated plants, and in addition they exert a plant growth-regulating action.

A particularly preferred field of use is the selective control of, chiefly, dicotyledonous weeds in cereal crops, particularly in rice.

Although the novel active substances of the formula I are effective in pre- and post-emergent application, the post-emergent application as contact herbicide is preferred, but the pre-emergent use is also of interest.

The novel active compounds, formulated for example as 25% wettable powders or for example, as emulsifiable concentrates, and diluted with water, are preferably applied to the crops of plants in the post-emergent stage.

Herbicidal action on applying the active compounds after emergence of the plants (post-emergent application)

Different cultivated plants and grass-like weeds are reared from seeds in pots in a greenhouse until they have reached the 4- to 6-leaf stage. Then the plants are sprayed with aqueous active substance emulsions (obtained from a 20% emulsifiable concentrate) in different rates of application. The treated plants are then kept at optimum light, watering, temperature (22°–25° C.) and humidity (50–70% relative humidity) conditions. Evaluation of the test was made 15 days after treatment.

In this test, compound 1 severely damaged all the dicotyledonous plants and weeds tested, whereas monocotyledonous cultures were largely unharmed and the grass-like weeds suffered only slight to medium-severe damage.

Selective herbicidal action on rice in the post-emergent procedure

Twenty-five-day-old rice plants are transplanted into large rectangular asbestos cement containers in a greenhouse. Seeds of the weeds occurring in rice crops, namely *Echinochloa crus galli, Sagittaria pygm., Cyperus difformis,* Ammania and Rotala, are then sown between the rows of rice plants. The containers are well watered and kept at a temperature of about 25° C. and at high humidity. Twelve days later, when the weeds have emerged and reached the 2–3 leaf stage, the soil in each of the containers is covered with a layer of water to a height of 2.5 cm. The active substance is then applied in the form of an emulsion concentrate with a pipette, or else in granule form, between the rows of plants. The emulsifiable concentrate is diluted and applied so that it corresponds to a field application rate of 2 and 1 kg respectively of active substance per hectare. The test is evaluated 4 weeks later. In this test, compound 1 severely damaged the dicotyledonous weeds Ammania and Rotala, as well as causing appreciable damage to the grass Cyperus. The rice remained undamaged.

The tested compounds of the present invention had a strong contact herbicidal action on some plants and in many others effected stationary growth as a symptom of the growth-inhibiting properties.

Growth inhibition in grasses

Seeds of the grasses *Lolium perenne, Poa pratensis, Festuca ovina,* and *Dactylis glomerata* were sown in plastic dishes filled with an earth/turf/sand mixture (6:3:1). The emergent grasses were cut back weekly to a height of 4 cm above the soil and 1 day after the last cut were sprayed with aqueous spray mixtures of an active substance of the formula I. The amount of active substance corresponded to a rate of application of 5 kg of active substance per hectare. The growth of the grasses was evaluated 10 and 21 days after application.

Growth inhibition in cereals

Spring wheat (*Triticum aestivum*), summer barley (*Hordeum vulgare*) and rye (Secale) was sown in sterilised soil in plastic beakers and reared in a greenhouse. The cereal shoots were treated 5 days after sowing with a spray broth of the active substance. The leaf application corresponded to 6 kg of active substance per hectare. Evaluation is made 21 days later. The active substances of the invention effect a marked growth inhibition both of grasses and cereal crops.

We claim:

1. The compound α-[3-(2',4'-dichlorophenoxy)-6-chlorophenylthio]-propionic acid 2"-methoxyethylamide.

2. The compound α-[3-(2',4'-dichlorophenoxy)-6-chlorophenylthio]-propionic acid 2"-hydroxyethylamide.

3. The compound α-[3-(2'-chloro-4'-trifluoromethylphenoxy)-6-chlorophenylthio]-propionic acid 2"-methoxyethylamide.

4. A herbicidal and plant growth-regulating composition which contains as active ingredient an effective amount of a phenoxyphenylthioalkanecarboxylic acid derivative of claims 1, 2 or 3, together with a suitable carrier therefor.

5. A method of combatting weeds at a locus which comprises applying to said locus an effective weed combatting amount of a compound of claims 1, 2 or 3.

6. A method of inhibiting plant growth which comprises applying to plants an effective plant growth inhibiting amount of a compound of claims 1, 2 or 3.

* * * * *